United States Patent
Bosy et al.

(10) Patent No.: US 11,530,941 B2
(45) Date of Patent: Dec. 20, 2022

(54) HEMATOCRIT AND LIQUID LEVEL SENSOR

(71) Applicant: Instrumentation Laboratory Company, Bedford, MA (US)

(72) Inventors: Brian Joseph Bosy, Hull, MA (US); Josef Kerimo, Concord, MA (US)

(73) Assignee: INSTRUMENTATION LABORATORY COMPANY, Bedford, MA (US)

( * ) Notice: Subject to any disclaimer, the term of this patent is extended or adjusted under 35 U.S.C. 154(b) by 1002 days.

(21) Appl. No.: 16/222,412

(22) Filed: Dec. 17, 2018

(65) Prior Publication Data
US 2020/0191636 A1    Jun. 18, 2020

(51) Int. Cl.
| | | |
|---|---|---|
| *G01F 23/24* | (2006.01) | |
| *A61B 5/145* | (2006.01) | |
| *G01N 15/05* | (2006.01) | |
| *G01N 33/49* | (2006.01) | |
| *G01N 35/10* | (2006.01) | |

(52) U.S. Cl.
CPC ........ *G01F 23/242* (2013.01); *A61B 5/14535* (2013.01); *G01F 23/243* (2013.01); *G01N 15/05* (2013.01); *G01N 33/491* (2013.01); *G01N 35/1011* (2013.01); *G01N 35/1016* (2013.01); *G01N 2035/1025* (2013.01)

(58) Field of Classification Search
CPC ...... G01F 23/242; G01F 23/241; G01F 23/24; G01F 23/22; G01F 23/243; A61B 5/14535; A61B 5/145; G01N 15/05; G01N 15/04; G01N 33/194; G01N 33/49; G01N 33/487; G01N 33/483; G01N 33/48; G01N 35/1011; G01N 35/1009; G01N 35/10

USPC .................................................. 422/106, 105
See application file for complete search history.

(56) References Cited

U.S. PATENT DOCUMENTS

| | | |
|---|---|---|
| 7,621,181 B2 | 11/2009 | Cammarata et al. |
| 7,992,437 B2 | 8/2011 | Tshishiku |
| 8,758,702 B2 | 6/2014 | Blouin et al. |
| 9,920,765 B2 | 3/2018 | Zimmerman |

(Continued)

FOREIGN PATENT DOCUMENTS

| | | |
|---|---|---|
| DE | 29609222 U1 | 10/1996 |
| WO | 2012/023902 A1 | 2/2012 |

OTHER PUBLICATIONS

Moeller Feinmechanik GMBH & CO, English Machine Translation of DE 296 09 222 U1 Description, 1996, obtained on Mar. 22, 2022 from espacenet.com (Year: 1996).*

(Continued)

*Primary Examiner* — Christine T Mui
(74) *Attorney, Agent, or Firm* — Burns & Levinson LLP

(57) ABSTRACT

A fluid aspiration probe apparatus for automatic fluid testing equipment includes a pair of electrodes mounted on a distal probe tip. The electrodes are coupled to an impedance measurement apparatus via conductive pathways along the probe. The impedance measurements and probe tip height are monitored as the probe tip is lowered into a fluid sample. Boundaries between layers of fluid in the container are detected by recognizing sudden changes in the impedance measurements and heights of the boundaries are determined by tracking the position of probe tip when the sudden changes of impedance occur.

20 Claims, 12 Drawing Sheets

(56) References Cited

U.S. PATENT DOCUMENTS 9,945,712 B2 4/2018 Kenney et al.
2011/0116967 A1* 5/2011 Roy .................... H05H 1/2406
422/186.05

OTHER PUBLICATIONS

International Search Report and Written Opinion for International Application No. PCT/US2019/065636, dated Jun. 25, 2020, 19 pages.
International Preliminary Report on Patentability dated Jul. 1, 2021 for International Application No. PCT/US2019/065636, 13 pgs.
Yun et al.,"Improvement of Depth Profiling into Biotissues Using Micro Electrical Impedance Spectroscopy on a Needle with Selective Passivation" Sensors, 16:2207 (2016).
Magnetrol, "Liquid Interface Level Measurement: Special Application Series", 8 pages, Sep. 2018.

* cited by examiner

HEMATOCRIT AND LIQUID LEVEL SENSOR

FIELD OF TECHNOLOGY

The present disclosure is in the field of laboratory automation systems and more particularly in the field of automated hemostasis testing systems.

BACKGROUND

Point of care laboratory automation systems are commonly used to perform multiple tests of bodily fluid samples. Presently used hemostasis testing systems, such as the ACL TOP family of testing systems by Instrumentation Laboratories of Bedford, Mass. perform automated measurements on blood samples that have been subjected to centrifugation.

Presently available automated hemostasis testing systems generally require the fill levels of samples in sample collection tubes to be accurate within a small margin of error. For example, the sample collection tubes used in the ACL TOP family of instruments should be filled to within +/−10% of a specified fill level in order to avoid negative effects on test results. Incorrect sample volumes or extreme blood hematocrit levels can result in incorrect anti-coagulant-to-sample ratios or other system errors that would cause inaccurate test results, for example.

FIG. 1 shows three sample collection tubes with different hematocrit levels after centrifuging a whole blood sample 100. The three sample collection tubes include centrifuged plasma content of test tubes with a normal hematocrit level 102, a reduced hematocrit level 104 and an increased hematocrit level 106. A thin layer called a buffy later is generally present between the plasma and the red blood cell layer.

The plasma layers 108 and red blood cell layers 110 vary considerably in the field. In the presently available hemostasis testing instruments, centrifuged blood samples with very high or very low hematocrit levels can introduce errors in test results. Accordingly, an important goal in the field of automated hemostasis testing systems is to automatically distinguish between centrifuged the centrifuged blood samples with different hematocrit levels and to detect the respective heights of the plasma layer and the red blood cell layer in a centrifuged blood sample.

Standard methods for measuring the hematocrit level in a blood sample involve centrifuging the blood sample in a sample tube and optically measuring the height of the different layers in the resulting centrifuged blood using infrared sensing, for example. However, the standard optical measurement methods do not work well with presently used sample tubes because the sample tubes are typically covered with numerous labels or may be otherwise incompatible with optical measurement apparatus.

FIG. 2 shows an example of a typical sample collection tube 202 used in a hemostasis testing system. The sample collection tube 202 has multiple labels 204 attached, which include essential information for the testing system. The labels 204 can obscure and prevent optical or visual inspection of the sample collection tube contents, for example.

Some presently available hemostasis testing instruments include a sensor that measures sample volume. However these instruments generally lack an ability to detect hematocrit level in the sample by detecting the heights of the separated plasma and red blood layers. Present testing methods generally do not introduce a sensor into a centrifuged sample near the red blood cell layer to avoid perturbing the sample and mixing any of the red blood cell layer with the plasma layer, for example.

SUMMARY

Aspects of the present disclosure include a method and apparatus for sensing the hematocrit level and fill level in a sample collection tube based on impedance measurements of the centrifuged sample in the sample collection tube.

Electrical impedance measurements have previously been used to estimate the hematocrit of a whole blood sample by measuring the electrical impedance between a pair of electrodes immersed in the sample. The measured value of the electrical impedance in each sample is compared to a table of impedance values correlated to corresponding hematocrit levels in order to estimate the hematocrit level of each sample, for example. These methods do not provide sample fill levels, or the respective levels of plasma and red blood cells in a container of centrifuged blood, for example.

According to an aspect of the present disclosure electrical impedance measurements between a pair of electrodes are performed to detect the plasma layer and red blood cell (RBC) layer of a centrifuged blood sample. The electrodes are mounted or integrated at the tip of a probe that is inserted by a linear actuating mechanism into the centrifuged blood sample. Because the electrical impedances of air, plasma, and red blood cells are very different from each other, the height of the different layers can be clearly detected as sudden changes in impedance when electrodes in the disclosed sensor reaches a boundary between the different layers.

The electrical impedance between the electrodes and the vertical displacement of the probe tip relative to a datum are monitored and/or recorded while the probe is being inserted into the sample. When a substantial change in impedance, i.e., an impedance change exceeding a predetermined threshold between the electrodes is measured, the vertical displacement of the probe tip relative to the datum is determined to indicate the height or level of a boundary between layers. For example, as the probe is being lowered into the sample container containing centrifuged blood, a first boundary to be detected is a boundary between air and plasma, which indicates the sample fill level. A second boundary to be detected may be a boundary between the plasma layer and the red blood cell layer. The second boundary thereby indicates the hematocrit height level of the centrifuged sample.

According to an aspect of the present disclosure, the probe including the pair of electrodes and conductive pathways along the probe to the electrodes are streamlined to minimize perturbation of the plasma layer or the red blood cell layer in a centrifuged sample. Fluidic pressure exerted by the probe on a fluid sample is minimized by minimizing the size and cross-section the probe apparatus including the electrodes and conductive pathways, for example. Moreover, according to an aspect of the present disclosure, the probe may be lowered very slowly as it approaches the second boundary, and stopped suddenly to minimize contact with the red blood cell layer as soon the second boundary is recognized by a detected impedance change between the electrodes.

According to this aspect of the present disclosure, it is important that the electrodes are very small and mounted very close to the distal end of the probe. In an illustrative embodiment, the electrodes are within about 0.2 millimeters of the probe tip. In another embodiment, the electrodes are on a distal facing surface of the probe tip. In another illustrative embodiment, the electrodes are formed as gold plated pads having a diameter or side length of about 0.001 inches.

According to aspects of the present disclosure, hematocrit height measurements techniques are much simpler and more accurate than the previously known techniques for hematocrit measurement of whole blood for at least the reason that the disclosed method can more easily detect the very different impedances of two extreme levels of hematocrit (0% hematocrit for the plasma layer and 100% hematocrit for the red blood cell layer), whereas the previously known hematocrit testing methods have relied on distinguishing smaller increments hematocrit based on correlated incremental levels electrical impedance. For at least this reason, the disclosed method and apparatus is comparatively very sensitive and can report more accurate values for the plasma and red blood cell level and provide more accurate hematocrit measurements.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principals of the present disclosure.

DETAILED DESCRIPTION

Figure 1:
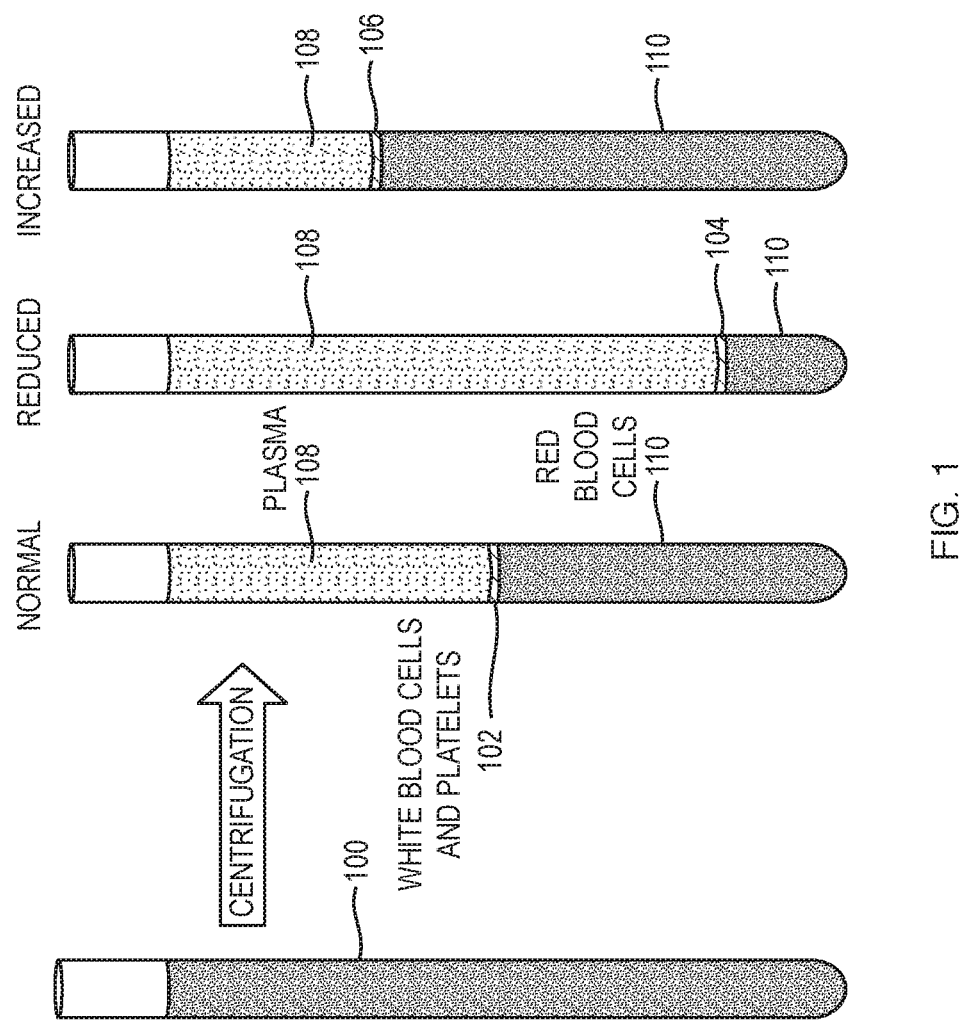
FIG. 1 is a drawing showing examples of centrifuged blood samples having varying hematocrit levels.
Figure 2:
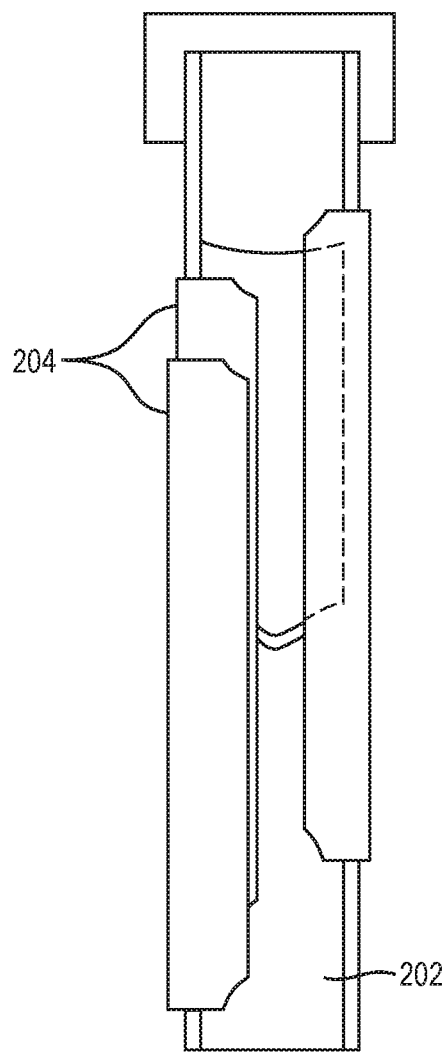
FIG. 2 is a drawing showing an example of blood sample container labeling that can obstruct previously known optical fluid measurement techniques.

A probe apparatus for determining one or more characteristic of a fluid according to an aspect of the present disclosure is described with reference to FIGS. 3-7. The apparatus includes a generally cylindrical fluid aspiration probe 304 having an internal bore 301 configured for aspirating a fluid therethrough. The fluid aspiration probe 304 described herein may be similar in shape and in certain mechanical aspects to a fluid aspiration probe for use in a closed tube sampling assembly as described in U.S. Pat. No. 8,758,702, which was granted to Instrumentation Laboratories of Bedford, Mass., for example.

According to an aspect of the present disclosure, a pair of insulated conductive paths 310 are provided on a surface of the fluid aspiration probe 304. The insulated conductive paths 310 extending from a distal end 303 of fluid aspiration probe 304 to a proximal end 305 of the fluid aspiration probe 304. The pair of insulated conductive paths are substantial conformal with the surface of the aspiration probe such that the insulated conductive paths do not significantly affect streamlining of a probe shape in a way that could increase fluid resistance against the probe or increase perturbation of fluids when the fluid aspiration probe is inserted therein.

According to an aspect of the present disclosure, the two isolated miniature electrodes 302 are mounted and/or integrated at the distal end of a fluid aspiration probe 304. The disclosed apparatus performs impedance-based hematocrit measurements by measuring the height of the probe tip inside of a sample tube when impedance changes between the electrodes 302 are detected. In the example shown in FIG. 3, the fluid aspiration probe 304 is disposed coaxially within a septum piercing sheath 306, as used in the presently known TOP system.

Figures 3A, 3B:
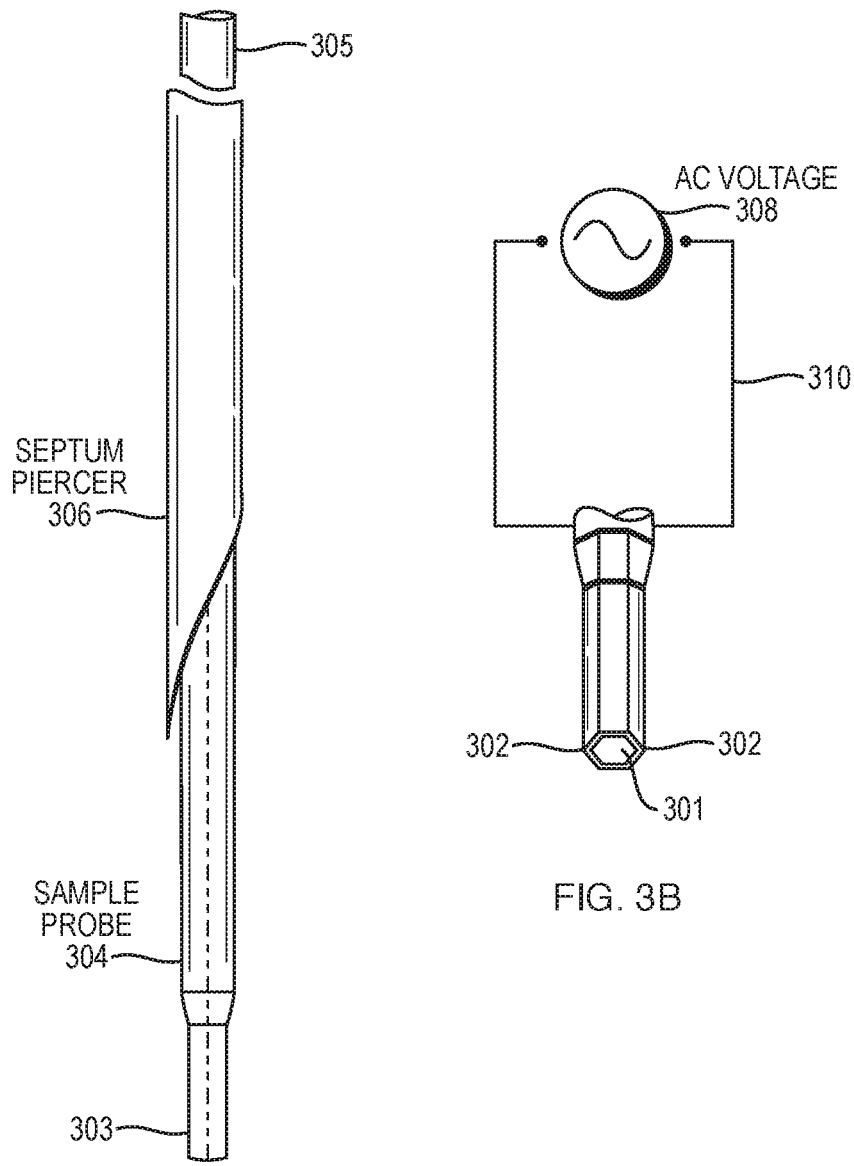
FIG. 3a is a drawing of a fluid aspiration probe according to an aspect of the present disclosure.
FIG. 3b is a drawing of conductive paths coupling a power source to a pair of electrodes formed on a fluid aspiration probe tip according to an aspect of the present disclosure.

Referring to FIG. 3(b) an expanded view of the distal end of the fluid aspiration probe 304 is shown where the two electrodes 302 are located. The electrodes 302 are placed as close as possible to the distal tip of the probe 304 to minimize the disturbance of the red blood cell (RBC) layer as measurements are performed. According to an aspect of the present disclosure, the electrodes 302 are separately coupled to an alternating current (AC) voltage source 308 via respective insulated conductive paths 310. The AC voltage source 308 provides a constant amplitude AC voltage to the electrodes 302 so that a voltage drop across the electrodes 302 can be measured in lieu of or representative of an electrical resistance measurement across the electrodes 302.

As the electrodes 302 are immersed through a boundary between different fluids the electrical impedance measured between the electrodes 302 changes dramatically. In an example implementation as the electrodes were moved from air to plasma the voltage drop representing impedance between the electrodes 302 changed from 0 millivolts to 900 millivolts. Then as the electrodes 302 were moved lower from the plasma layer into the red blood cell layer, the voltage drop between the electrodes 302 changed from 900 millivolts to 450 millivolts.

According to an aspect of the present disclosure, the disclosed sensor apparatus can be implemented to measure hematocrit levels containers that are closed with a septum. In these implementations the fluid aspiration probe 304 can be retracted and protected within the septum piercing sheath 306 while the septum piercing sheath 306 pierces the septum and allows the fluid aspiration probe 304 and electrodes 302 to safely enter the closed container. Once the septum piercing sheath 306 has been extended through the container septum, the fluid aspiration probe 304 can be safely extended from the septum piercing sheath into the container.

In one illustrative embodiment, the pair of insulated conductive paths are deposited on an insulated substrate layer on the surface of the fluid aspiration probe, for example. For example, according to an aspect of the present disclosure, an insulating substrate layer, a conductive layer over the substrate and an insulating top layer over the conductive layer may be deposited directly on the surface of the fluid aspiration probe using thin film vapor deposition techniques to form the pair of insulated conductive paths.

Figure 6:
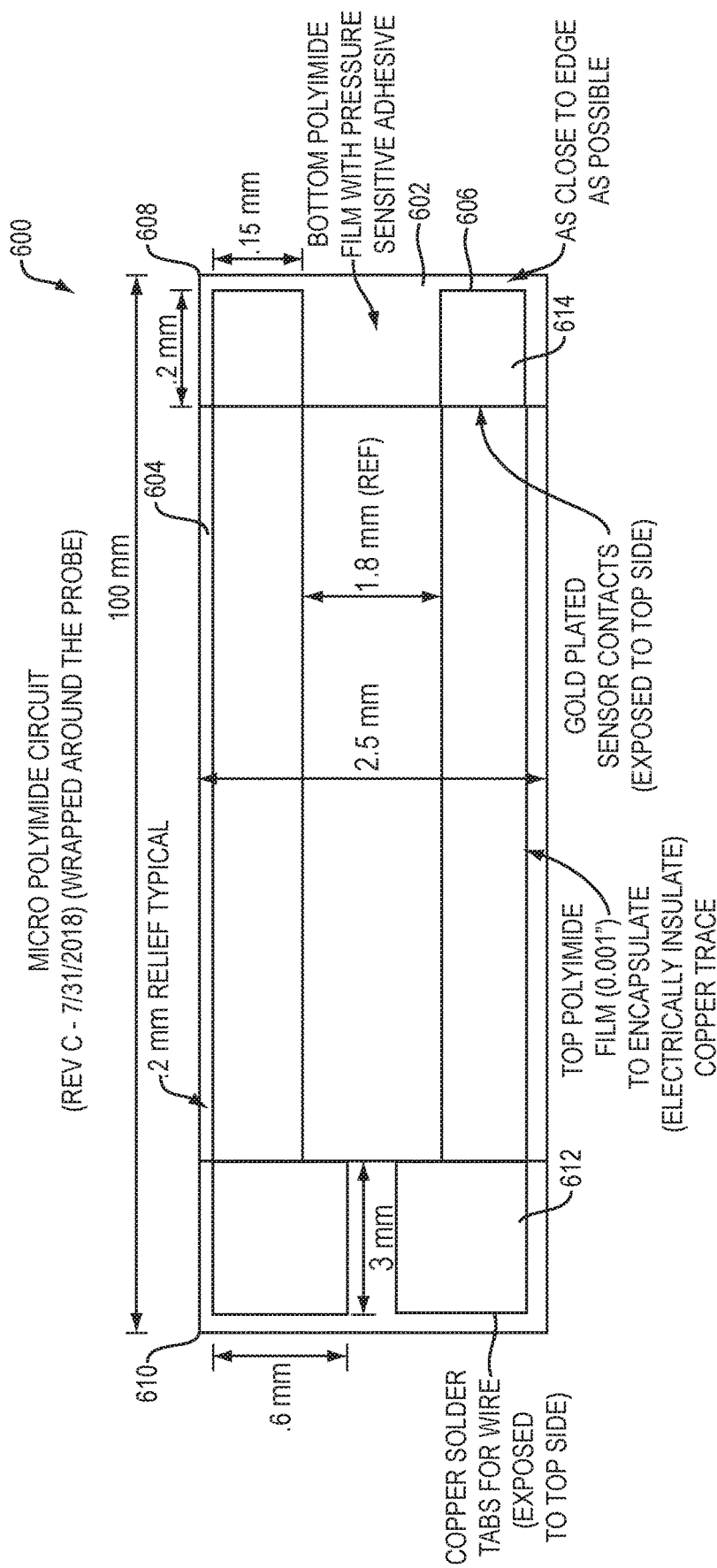
FIG. 6 is a drawing showing a flexible tape for providing conductive pathways along a fluid aspiration probe according to aspects of the present disclosure.

In another embodiment, a flexible tape containing the insulated conductive paths is adhered to the surface of the fluid aspiration probe. Referring to FIG. 6, in the illustrative embodiment, the flexible tape 600 includes a pair of polyimide layers 602, 604 and a number of copper traces 606 between the pair of polyimide layers 602, 604.

One of the polyimide layers is an insulating substrate film layer 602. The conductive traces 606 are formed on a first surface of the insulating substrate film layer 602 and extend from a distal end 608 of the flexible tape 600 to a proximal end 610 of the flexible tape. A pressure sensitive adhesive is provided on a second surface of the substrate film layer 602, i.e., on the back of the flexible tape 600, for adhering the flexible tape to the outer surface of the fluid aspiration probe 304 (FIG. 3).

The other one of the polyimide layers is an insulating outer layer 604 extending along the flexible tape over the conductive traces 606. The insulating outer layer 604 insulates the pair of conductive traces 606 and forms the pair of insulated conductive paths 310 (FIG. 3).

An exposed distal end portion 614 of the conductive traces 606 extends distally beyond a distal end of the insulating outer layer 604, and an exposed proximal end portion 612 of the conductive traces 606 extending distally beyond a proximal end of the insulating outer layer 604. In one example, the exposed proximal end portion 612 of the conductive traces are widened to form copper pads for soldering wires thereto.

According to an aspect of the present disclosure, a gold plated surface is formed on the exposed distal end portion 614 of each of the conductive traces. In an illustrative embodiment, the gold plated surfaces form a pair of electrodes for measuring electrical impedance therebetween via the insulated conductive paths 606.

The flexible tape 600 is adhered to the fluid aspiration probe 304 (FIG. 3). In the illustrative embodiment the flexible tape 600 extends longitudinally along the fluid aspiration probe surface and is extends laterally around the fluid aspiration probe 304. According to an aspect of the present disclosure, the insulated conductive paths are spaced apart from each other by 180 degrees of the aspiration probe circumference such that the exposed distal ends 614 of the conductive traces 606 are on opposite sides of the aspiration probe tip. In an illustrative embodiment the fluid aspiration probe 304 has a diameter of 1.2 mm such that in this embodiment, the electrodes are only 1.2 mm apart from each other.

In one embodiment, the pair of electrodes are located adjacent to the distal end of the fluid aspiration probe, e.g. within about 0.02 millimeters of the distal tip. In another embodiment, the pair of electrodes are located on the distal facing surface of the fluid aspiration probes distal end.

Figure 4:
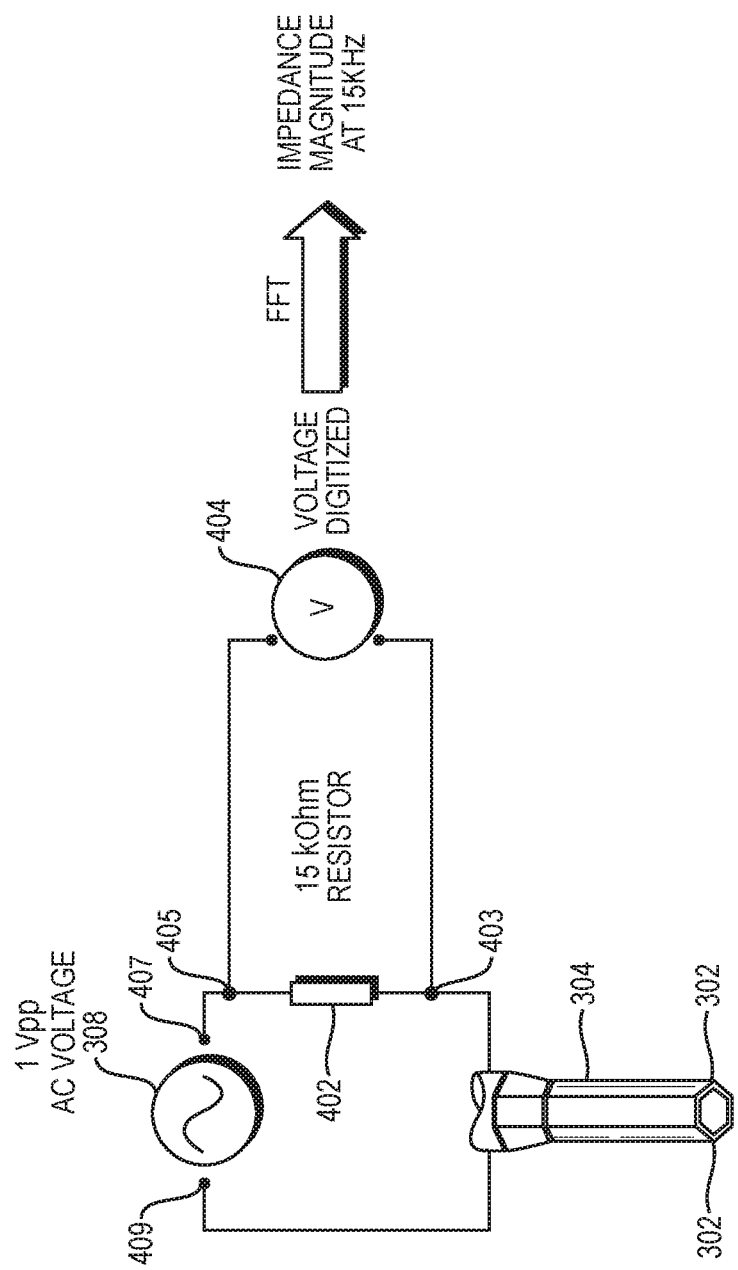
FIG. 4 is a schematic drawing showing impedance measuring circuitry coupled to a fluid aspiration probe apparatus according to an aspect of the present disclosure.

Referring to FIG. 4, an embodiment of the disclosed apparatus also includes a resistor 402 having a first terminal 403 and a second terminal 405 and a voltage source 308 having a first terminal 407 and a second terminal 409. The first terminal 403 of the resistor 402 is coupled a first one of the conductive traces 310 and the second terminal 405 of the resistor 402 is coupled to the first terminal 407 of the voltage source 308. The second terminal 409 of the voltage source 308 is coupled to a second one of the conductive traces 310. A voltage measurement apparatus 404 is coupled to the first terminal 405 of the resistor 402 and the second terminal 405 of the resistor 402, and configured for measuring a voltage drop therebetween.

In this example, the resistor has a value of 15 kilo-ohms and the voltage source 308 is a alternating current (AC) voltage source having an amplitude of 1 volt peak to peak and a frequency of 15 kilohertz. The voltage drop across the resistor 402 can be measured by the voltage measurement device 404 such as an oscilloscope or digital voltmeter in lieu of or representative of impedance between the electrodes 302.

Figure 5:
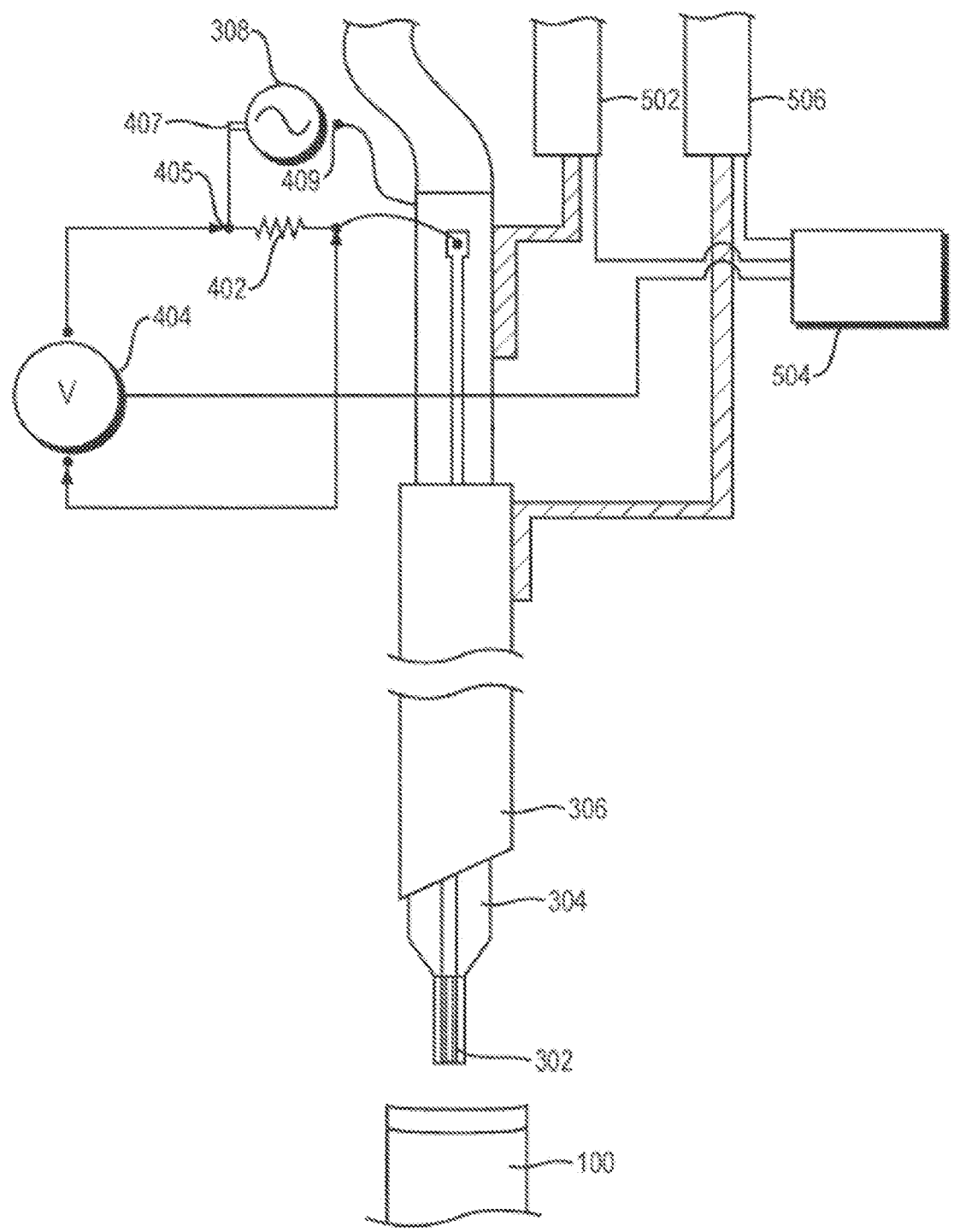
FIG. 5 is a schematic drawing showing motion control circuitry and impedance measurement circuitry coupled to a fluid aspiration probe apparatus according to an aspect of the present disclosure.

Referring to FIG. 5, according to another aspect of the present disclosure, a first linear actuator 502 is mechanically coupled to the fluid aspiration probe 304. Motion controller circuitry 504 is coupled to the first linear actuator 502 and to the voltage measurement apparatus 404. The first linear actuator 502 is configured to displace the fluid aspiration probe 304 vertically within a fluid container 100 in response to motion signals received from the motion controller circuitry 504. According to an aspect of the present disclosure, the motion controller circuitry 504 is configured to monitor and report vertical displacement of the fluid aspiration probe 304 when changes exceeding a predetermined threshold in the electrical impedance between the pair of electrodes 302 are determined based on measurements by the voltage measurement apparatus 404.

According to an aspect of the present disclosure, the first linear actuator 502 comprises a stepper motor coupled to the fluid aspiration probe 304 and a step counter configured for counting steps of the stepper motor. The steps of the stepper motor are correlated to a vertical displacement of the fluid aspiration probe 304.

In an illustrative embodiment, an external sleeve 306 at least partially sheaths the fluid aspiration probe 304 and is configured for piercing a septum of the container 100. The fluid aspiration probe 304 is movable vertically relative to the external sleeve 306. For example, as shown in FIG. 5, the external sleeve 306 may be mechanically coupled to a second linear actuator 506 which is also coupled to and controlled by the motion controller circuitry 504.

In another illustrative embodiment a transducer (not shown) is coupled to the pair of insulated conductive paths 310 on the distal end 303 of the fluid aspiration probe 304 in addition to or instead of the electrodes 302. The transducer may be a temperature sensor; a pressure sensor; a capacitance sensor or other sensor, for measuring fluid characteristics such as the amount of protein in blood plasma, for example.

Figure 7:
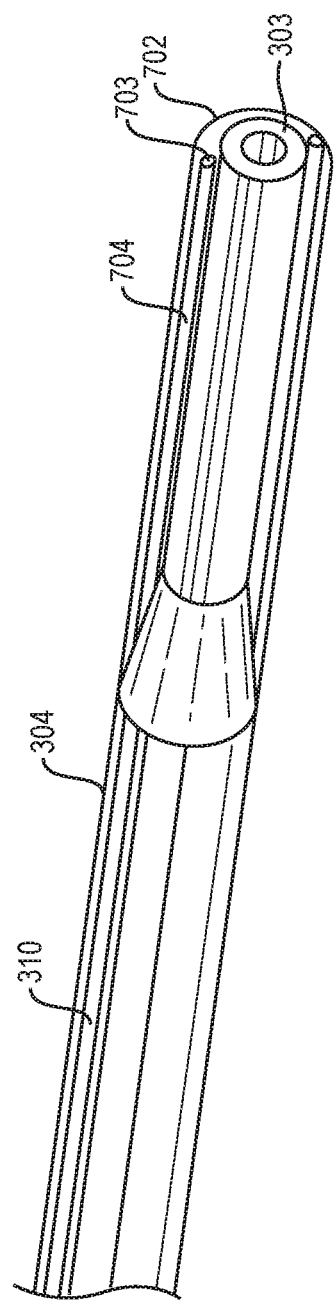
FIG. 7 is a drawing showing a collar for mounting distal facing electrodes to a probe tip according to an aspect of the present disclosure.

Referring to FIG. 7, in an illustrative embodiment, the disclosed apparatus includes an insulating collar member 702 disposed around the distal end 303 of the fluid aspiration probe 304. In this embodiment, a pair of electrodes 703 are disposed on a distal facing surface of the collar member. The insulating collar member 702 may be molded from an insulating polymer material, for example. The electrodes 703 and/or sensors, for example, may be formed or installed on a distal facing surface of the insulating collar member 702, and electrically coupled to the insulated conductive paths 310 via conductive pathways 704. The conductive pathways 704 may be implemented as pins or other conductive members installed in the insulating collar member 702 or molded into the insulating collar member 702, for example.

Methods for aspirating a centrifuged fluid sample and determining the hematocrit level in a container of centrifuged blood using the disclosed aspiration probe apparatus according to aspects of the present disclosure are described with reference to FIGS. 8-11.

Figure 8:
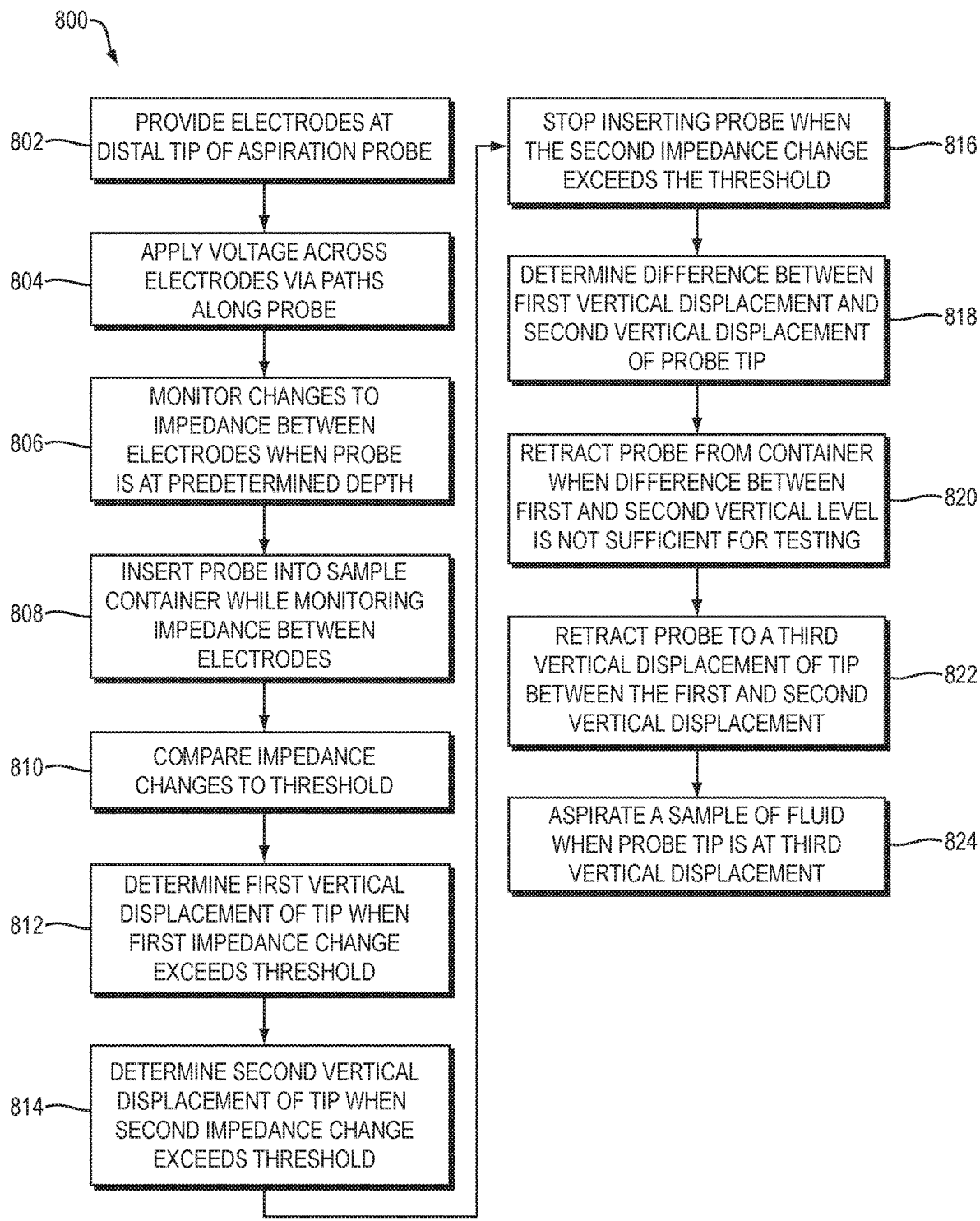
FIG. 8 is a process flow diagram showing a method for aspirating a centrifuged fluid sample from a container according to an aspect of the present disclosure.

A method 800, for aspirating a centrifuged fluid sample from a container according to an aspect of the present disclosure is described with reference to FIG. 8. At step 802, the method 800 includes providing a pair of electrodes at a distal dip of a fluid aspiration probe. At step 804, the method 800 includes applying an electrical voltage across the pair of electrodes via a pair of insulated conductive paths extending from the distal tip to a proximal end of the fluid aspiration probe. At step 806, the method 800 includes monitoring changes to an electrical impedance between the electrodes via the pair of insulated conductive paths when the probe is at the predetermined depth and the electrical voltage is applied. At step 808, the method 800 includes inserting the probe into a fluid sample container while the electrical voltage is applied and while monitoring the changes to the electrical impedance. At step 810, the method 800 includes comparing the changes to the electrical impedance with a predetermined threshold of changes of electrical impedance. At step 812, the method 800 includes determining a first vertical displacement of the distal tip relative to a datum when a first change to the electrical impedance exceeding the predetermined threshold is detected, wherein the first change occurs at a first fluid boundary.

In an illustrative embodiment, the fluid sample container contains a blood sample. According to another aspect of the present disclosure, the method 800 may include centrifuging the blood sample prior to inserting the probe into the fluid sample container.

In an illustrative embodiment, the probe is retracted from the container when the first change to the electrical impedance exceeding the predetermined threshold is not detected before the probe tip reaches a predetermined first abort depth. According to an aspect of the present disclosure, when the first change to the electrical impedance exceeding the predetermined threshold is not detected before the probe tip reaches a predetermined first abort depth, a first alert signal is provided to indicate that the total fluid level in the container is too low. According to another aspect of the present disclosure, when the first change to the electrical impedance exceeding the predetermined threshold is detected before the probe tip reaches a predetermined maximum fill height an overfill alert signal is provided indicating the total level in the container is too high. The process of aspirating the centrifuged fluid sample may be aborted for containers in which the total fluid level in the container has been determined as being either too low or too high.

At step 814, the method 800 includes determining a second vertical displacement of the distal tip relative to the datum when a second change to the electrical impedance exceeding the predetermined threshold is detected, wherein the second change occurs at a second fluid boundary. According to an aspect of the present disclosure, the changes in the electrical impedance measurements occur when the pair of electrodes transit boundaries between fluids in the container. In the illustrative embodiment, the fluid sample container contains a centrifuged blood sample having a plasma layer separated from a red blood cell layer at the second fluid boundary therebetween, and the plasma layer is separated from ambient air at the first fluid boundary. In this example, the first fluid boundary is a boundary between an ambient gas layer and layer of blood plasma, and the second fluid boundary is a boundary between the layer of blood plasma and a layer of red blood cells.

In an illustrative embodiment, the probe is retracted from the container when the second change to the electrical impedance exceeding the predetermined threshold is not detected before the probe tip reaches a predetermined second abort depth. According to an aspect of the present disclosure, when the second change to the electrical impedance exceeding the predetermined threshold is not detected before the probe tip reaches a predetermined second abort depth, a second alert signal is provided to indicate a second fluid (e.g. a red blood cell level in the container) is too low.

At step 816, the method 800 includes stopping the inserting of the probe when the second change to the electrical impedance exceeding the predetermined threshold is detected at the second fluid boundary.

At step 818, the method 800 includes determining a difference between the first vertical displacement of the probe tip and the second vertical displacement of the probe tip. At step 820, the method 800 includes retracting the probe from the container when a difference between the first vertical displacement and the second vertical displacement is determined as not exceeding a predetermined minimum first fluid layer thickness.

In an illustrative embodiment, a third alert signal is provided to indicate insufficient volume of a first fluid (i.e. blood plasma) when a difference between the first vertical displacement and the second vertical displacement is determined as not exceeding a predetermined minimum first fluid layer height.

At step 822, the method 800 includes retracting the probe to a third vertical displacement of the probe tip between the first vertical displacement and the second vertical displacement after stopping the inserting of the probe. At step 824, the method 800 includes aspirating a sample of fluid from the container through the aspiration probe when the probe is retracted to the third vertical displacement of the probe tip.

According to an aspect of the present disclosure, a sheath is provided around the fluid aspiration probe. The sheath is aligned coaxially with the fluid aspiration probe and the fluid aspiration probe is controllably displaceable within the sheath along a central longitudinal axis of the sheath and the probe. In an illustrative embodiment of the disclosed method 800, the sheath is inserted to a predetermined sheath depth in the fluid sample container. The sheath pierces a cover of the fluid sample container creating a shielded pathway through the cover for extending the fluid aspiration probe through. In this illustrative embodiment, the step 808 of the inserting the probe into the fluid sample container includes extending the probe from a distal end of the sheath after the sheath pierces the cover of the fluid sample container.

According to another aspect of the present disclosure, the method 800 includes coupling a linear actuator to the probe, wherein the linear actuator includes a stepper motor. The method 800 may also include coupling controller circuitry to the linear actuator, in which the controller circuitry includes a processor and memory, and in which the memory stores program code executable by the processor to control the linear actuator for the inserting and the retracting of the probe.

Figure 9:
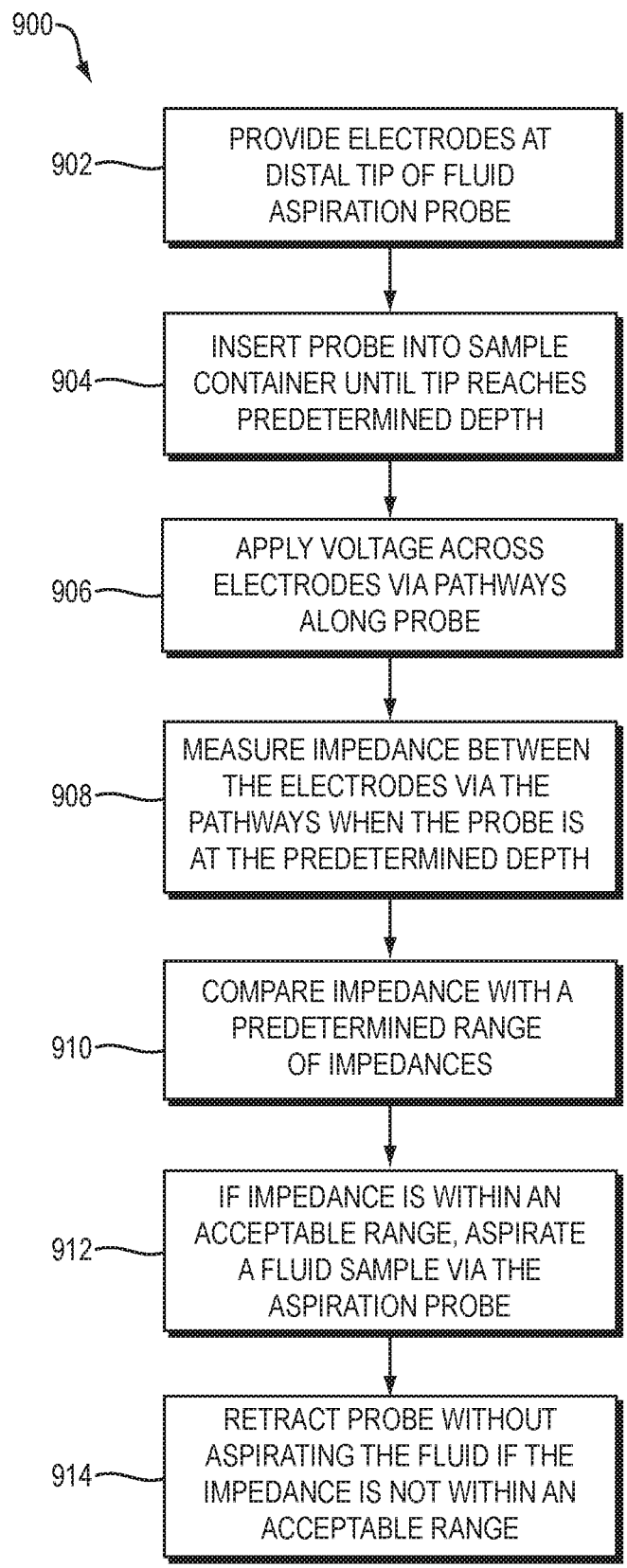
FIG. 9 is a process flow diagram showing another method for aspirating a centrifuged fluid sample from a container according to an aspect of the present disclosure.

Another method 900, for aspirating a centrifuged fluid sample from a container according to an aspect of the present disclosure is described with reference to FIG. 9. At step 902, the method 900 includes providing a pair of electrodes at a distal dip of a fluid aspiration probe. At step 904, the method 900 includes inserting the probe into a fluid sample container until the distal tip is at a predetermined depth. At step 906, the method 900 includes applying an electrical voltage across the pair of electrodes via a pair of insulated conductive paths extending from the distal tip to a proximal end of the fluid aspiration probe. At step 908, the method 900 includes measuring an electrical impedance between the electrodes via the pair of insulated conductive paths when the probe is at the predetermined depth and the electrical voltage is applied. At step 910, the method 900 includes comparing the electrical impedance with a predetermined range of impedance. At step 912, the method 900 includes aspirating a portion of a fluid sample from the container through the fluid aspiration probe when the electrical impedance is within the predetermined range. At step 914, the method 900 includes, retracting the fluid aspiration probe without aspirating a portion of the fluid sample from the container and providing an invalid sample signal when the electrical impedance is not within the predetermined range.

Figure 10:
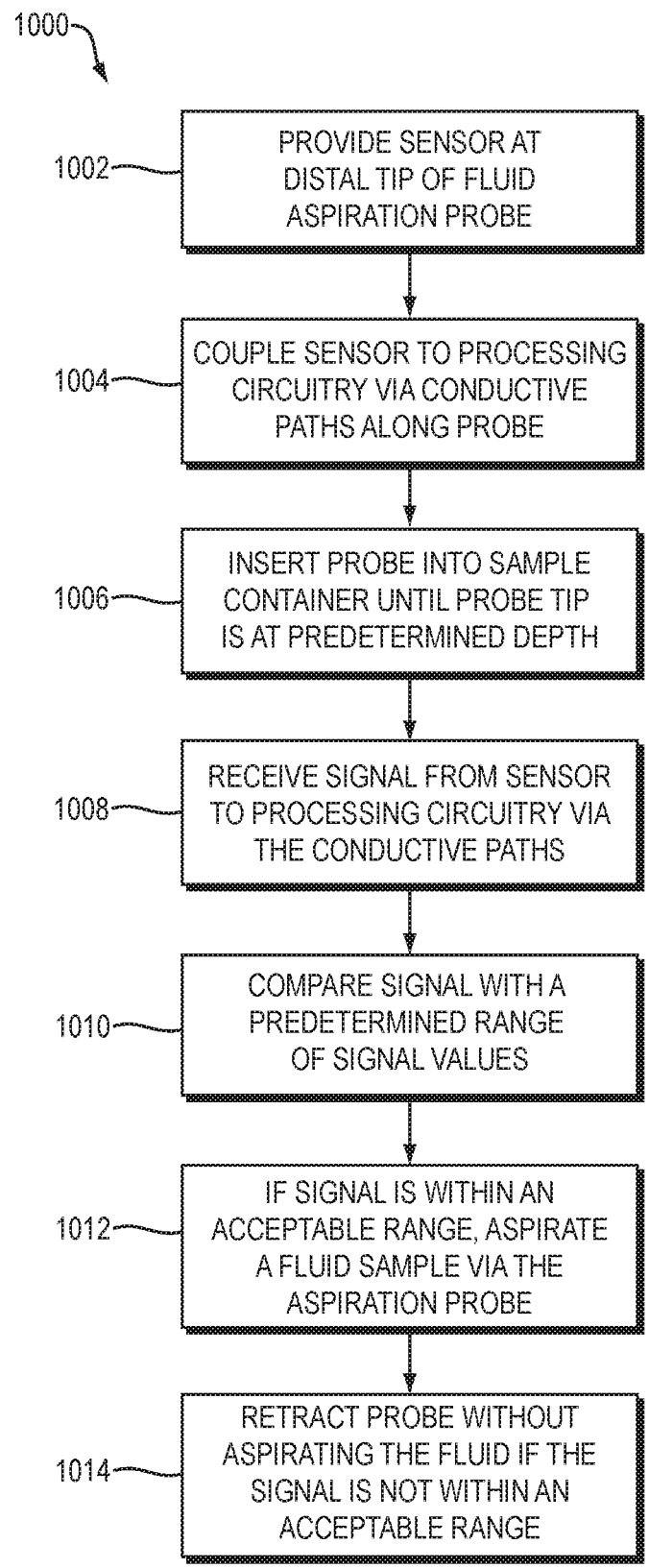
FIG. 10 is a process flow diagram showing another method for aspirating a centrifuged fluid sample from a container according to an aspect of the present disclosure.

Another method 1000, for aspirating a centrifuged fluid sample from a container according to an aspect of the present disclosure is described with reference to FIG. 10. At step 1002, the method 1000 includes providing a sensor at a distal dip of a fluid aspiration probe. At step 1004, the method 1000 includes coupling the sensor to processing circuitry via a plurality of insulated conductive paths extending from the distal tip to a proximal end of the fluid aspiration probe. At step 1006, the method 1000 includes inserting the probe into a fluid sample container until the distal tip is at a predetermined depth. At step 1008, the method 1000 includes receiving an electrical signal from the sensor by the processing circuitry via the pair of insulated conductive paths when the probe is at the predetermined depth. At step 1010, the method 1000 includes comparing the electrical signal with a predetermined range of electrical signal values. At step 1012, the method 1000 includes aspirating a portion of a fluid sample from the container through the fluid aspiration probe when the electrical signal is within the predetermined range.

At step 1014, the method 1000 includes retracting the fluid aspiration probe without aspirating a portion of the fluid sample and providing an invalid sample signal for the container when the electrical signal is not within the predetermined range.

Figure 11:
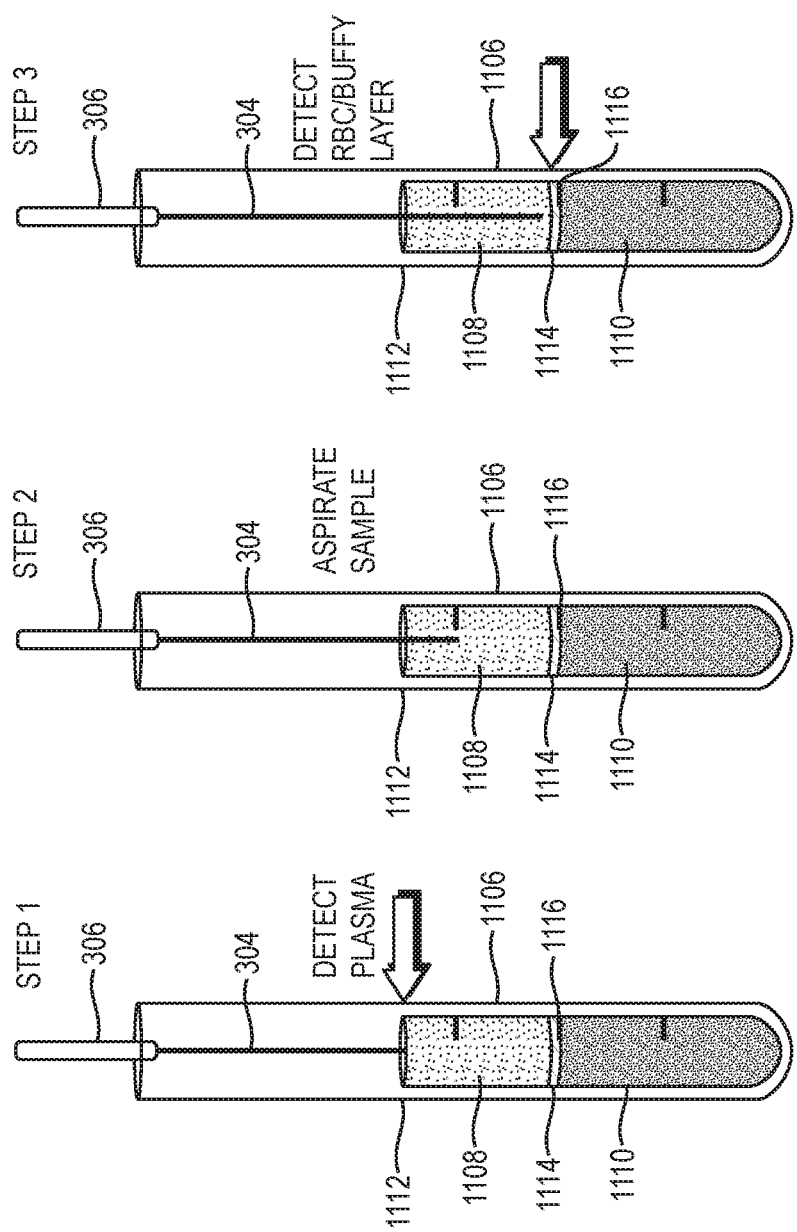
FIG. 11 is drawing showing steps of a method for detecting the layered interfaces inside a sample tube according to an aspect of the present disclosure.

An example of the disclosed method for detecting the layered interfaces inside a sample tube according to an aspect of the present disclosure is described with reference to FIG. 11. FIG. 11 shows a septum piercing sheath 306 and a fluid aspiration probe 304. In step 1 the container septum 1102 is pierced by the septum piercing sheath 306 to allow access to the interior of the sample container 1106. The fluid aspiration probe 304 is then unsheathed and lowered towards the plasma layer 1108 to detect the height of the top surface 1112 using the disclosed impedance sensing method and apparatus. In step 2, a predetermined plasma volume is pumped through the fluid aspiration probe 306 into the sample container 1106 for testing by an automatic testing instrument. In step 3, a height of the top surface 1114 of a red blood cell (RBC) layer 1110 or buffy coat layer 1116 is detected with the fluid aspiration probe using the disclosed apparatus and impedance monitoring methods disclosed herein, for example. According to an aspect of the present disclosure, a hematocrit level of the sample can be determined based on the heights detected in steps 1 and 3, for example.

Figure 12:
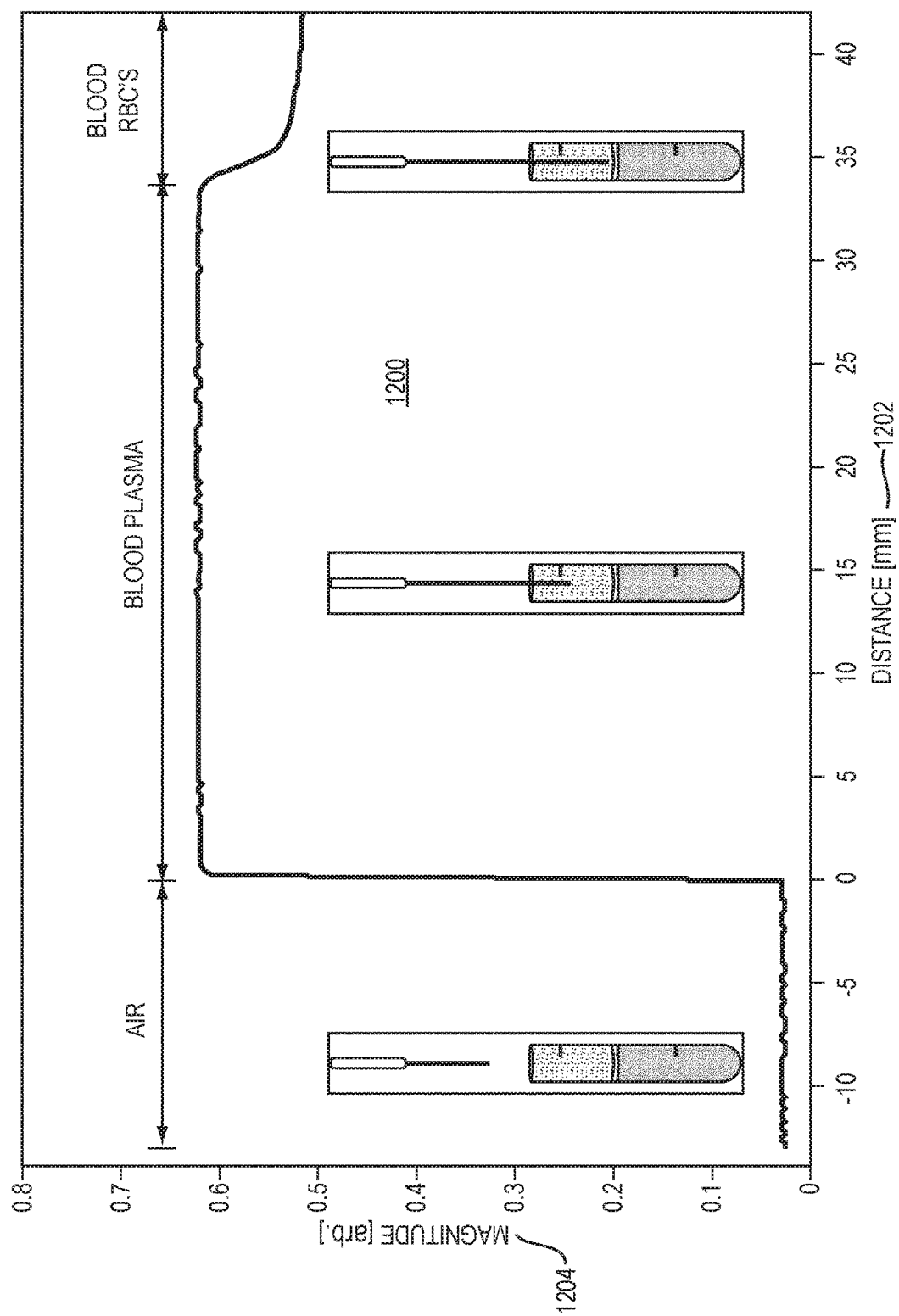
FIG. 12 is a graph of probe displacement versus measured impedance magnitude between the electrodes generated using the disclosed method and apparatus.

FIG. 12 shows a graph 1200 of probe displacement 1202 versus measured impedance magnitude 1204 between the electrodes on an arbitrary scale. The graph shows that as the probe is displaced from an initial position until it reaches the top surface of a plasma layer, the magnitude of measured impedance is approximately zero. When the probe firsts contacts a plasma layer, impedance between electrodes at the probe tip changes to about 0.63. According to an aspect of the present disclosure, the displacement measurement of the probe may be reset to zero millimeters to define a vertical displacement measurement datum. As the probe continues to be lowered the impedance measurement remains constant. Then when the probe has contacted a red blood cell layer, the impedance measurement suddenly changes to about 0.51. The graph shows the top surface of the plasma layer is about 33 millimeters above the top of the red blood cell layer.

The disclosed hematocrit sensor method and apparatus can be used to provide a pre-analytical sample quality check on a citrated sample collection tube. The sensor can notify the user of improper an anti-coagulant-to-sample ratios that can negatively affect the results. The disclosed hematocrit level and fill level sensing method and apparatus may be added to a set of pre-analytical checks already used on existing TOP instruments to improve the quality of results, for example.

Although the present invention is described by way of examples that employ electrical impedance sensing, it should be understood that various sensor sensors such as optical sensors, acoustic sensors and electrical detectors could potentially be used to determine the layered content of a centrifuged and obscured test tube according to aspects of the present disclosure. Examples of different sensor technologies that can be used to detect the different layers include: speckle imaging; near-infrared (NIR) absorption; ultrasound sensing; fiber optic sensor on probe for confocal detection; for example.

Although the present invention is described using the term "electrical impedance" it should be understood that various embodiments of the disclosed apparatus and method may be implemented by measuring electrical resistance, i.e. the resistive component of impedance and/or electrical reactance, (capacitance or inductance) i.e., the reactive components of impedance. The term "electrical impedance" as used herein should be understood to include electrical resistance, capacitance and/or inductance.

What is claimed is:

1. A probe for determining one or more characteristics of a fluid, the probe comprising:
   a fluid aspiration probe comprising an internal bore configured to aspirate the fluid through the internal bore;
   a pair of insulated conductive paths adjacent to a surface of the fluid aspiration probe, the pair of insulated conductive paths extending to a proximal end of the fluid aspiration probe; and
   flexible tape adhered to the surface of the fluid aspiration probe, the flexible tape containing the pair of insulated conductive paths;
   wherein the pair of insulated conductive paths are substantially conformal with the surface of the fluid aspiration probe.

2. The probe of claim 1, wherein the pair of insulated conductive paths are on an insulated substrate layer included in the flexible tape.

3. The probe of claim 1, wherein the flexible tape comprises:
   polyimide layers; and
   copper traces between the polyimide layers.

4. The probe of claim 1, wherein the flexible tape comprises:
   an insulating substrate film layer;

a pair of conductive traces on a first surface of the insulating substrate film layer and extending from a distal end of the flexible tape to a proximal end of the flexible tape;

a pressure sensitive adhesive on a second surface of the insulating substrate film layer, the first surface of the insulating substrate film layer being opposite the second surface of the insulating substrate film layer; and an insulating outer layer extending along the flexible tape over the pair of conductive traces, the insulating outer layer insulating the pair of conductive traces and forming the pair of insulated conductive paths.

5. The probe of claim 4, comprising:

an exposed distal end portion of each of the pair of conductive traces extending beyond a distal end of the insulating outer layer; and an exposed proximal end of each of the conductive traces extending beyond a proximal end of the insulating outer layer.

6. The probe of claim 5, further comprising:

a conductive surface formed on an exposed distal end portion of each of the conductive traces, where conductive surfaces on exposed distal end portions of the conductive traces comprise a pair of electrodes for measuring electrical impedance between the conductive traces.

7. The probe of claim 3, wherein the flexible tape extends longitudinally along the fluid aspiration probe surface and extends around the fluid aspiration probe.

8. The probe of claim 6, wherein the pair of insulated conductive paths are spaced apart from each other by 180 degrees on a circumference of the fluid aspiration probe such that the exposed distal end portions are on opposite sides of a tip of the fluid aspiration probe.

9. The probe of claim 6, further comprising:

a resistor having a first terminal and a second terminal, and a voltage source having a first terminal and a second terminal, wherein the first terminal of the resistor is coupled a first one of the conductive traces and the second terminal of the resistor is coupled to the first terminal of the voltage source, and wherein the second terminal of the voltage source is coupled to a second one of the conductive traces; and a voltage measurement apparatus coupled to the first terminal of the resistor and the second terminal of the resistor, and configured for measuring a voltage drop across the resistor.

10. The probe of claim 9, further comprising:

a linear actuator mechanically coupled to the fluid aspiration probe; and motion controller circuitry coupled to the linear actuator and to the voltage measurement apparatus;

wherein the linear actuator is configured to displace the fluid aspiration probe vertically within a container in response to motion signals received from the motion controller circuitry.

11. The probe of claim 10, wherein the motion controller circuitry is configured to monitor and to report vertical displacement of the fluid aspiration probe when changes exceeding a predetermined threshold in electrical impedance between the pair of electrodes are determined based on measurements by the voltage measurement apparatus.

12. The probe of claim 10, wherein the linear actuator comprises:

a stepper motor coupled to the fluid aspiration probe; and a step counter configured for counting steps of the stepper motor, wherein the steps of the stepper motor are correlated to a vertical displacement of the fluid aspiration probe.

13. The probe of claim 10, further comprising an external sleeve at least partially sheathing the fluid aspiration probe, the external sleeve being configured to pierce a septum of the container, wherein the fluid aspiration probe is movable vertically relative to the external sleeve.

14. The probe of claim 1, further comprising:

a transducer disposed on a distal end of the fluid aspiration probe, the transducer being coupled to the pair of insulated conductive paths.

15. The probe of claim 14, wherein the transducer comprises at last one of a temperature sensor, a pressure sensor, or a capacitance sensor.

16. The probe of claim 1, further comprising:

a sleeve at least partially sheathing the fluid aspiration probe, the sleeve being configured to pierce a septum of a container, the fluid aspiration probe being movable longitudinally relative to the sleeve.

17. The probe of claim 6, wherein the conductive surface comprises gold plating.

18. The probe of claim 1, wherein the fluid aspiration probe is generally cylindrical in shape.

19. The probe of claim of claim 3, wherein the polyimide layers comprise a pair of polyimide layers; and wherein one of the polyimide layers comprises an insulating substrate film layer.

20. The probe of claim 14, wherein the fluid comprises blood plasma and wherein the transducer is configured to measure an amount of protein in the blood plasma; or wherein the fluid comprises whole blood and wherein the transducer is configured to measure a hematocrit of the whole blood based on an electrical impedance between the pair of insulated conductive paths.

* * * * *